(12) United States Patent
McLawhorn

(10) Patent No.: US 10,022,178 B2
(45) Date of Patent: Jul. 17, 2018

(54) EXPANDABLE MESH PLATFORM FOR LARGE AREA ABLATION

(71) Applicant: Cook Medical Technologies LLC, Bloomington, IN (US)

(72) Inventor: Tyler E. McLawhorn, Winston-Salem, NC (US)

(73) Assignee: Cook Medical Technologies LLC, Bloomington, IN (US)

( * ) Notice: Subject to any disclaimer, the term of this patent is extended or adjusted under 35 U.S.C. 154(b) by 530 days.

(21) Appl. No.: 14/184,438

(22) Filed: Feb. 19, 2014

(65) Prior Publication Data

US 2014/0236146 A1 Aug. 21, 2014

Related U.S. Application Data

(60) Provisional application No. 61/767,067, filed on Feb. 20, 2013.

(51) Int. Cl.
*A61B 18/14* (2006.01)
*A61B 18/00* (2006.01)

(52) U.S. Cl.
CPC .......... *A61B 18/14* (2013.01); *A61B 18/1492* (2013.01); *A61B 2018/00267* (2013.01); *A61B 2018/00488* (2013.01); *A61B 2018/00577* (2013.01); *A61B 2018/1475* (2013.01)

(58) Field of Classification Search
CPC .. A61B 2018/0225; A61B 2018/00107; A61B 2018/0016; A61B 2018/00214; A61B 2018/00267
See application file for complete search history.

(56) References Cited

U.S. PATENT DOCUMENTS

| | | |
|---|---|---|
| 3,996,938 A | 12/1976 | Clark, III |
| 4,660,571 A | 4/1987 | Hess et al. |
| 5,255,679 A | 10/1993 | Imran |
| 5,311,866 A | 5/1994 | Kagan et al. |
| 5,397,341 A | 3/1995 | Hirschberg et al. |
| 5,797,903 A | 8/1998 | Swanson et al. |
| 5,836,874 A | 11/1998 | Swanson et al. |
| 6,163,716 A | 12/2000 | Edwards et al. |
| 6,283,987 B1 | 9/2001 | Laird et al. |

(Continued)

FOREIGN PATENT DOCUMENTS

GB 227 1932 5/1994

*Primary Examiner* — Jaymi Della
(74) *Attorney, Agent, or Firm* — Brinks Gilson & Lione

(57) ABSTRACT

An ablation device and a method of ablating a tissue are provided. The ablation device includes a first elongate shaft having a proximal portion, a distal portion and a lumen extending at least partially therethrough and a second elongate shaft having a proximal portion, a distal portion and a lumen extending at least partially therethrough. The first elongate shaft is coaxially positioned and longitudinally movable relative to the second elongate shaft. The ablation device further includes a mesh member including a proximal portion and a distal portion. The proximal portion of the mesh member is operably connected to the distal portion of the second elongate shaft and the distal potion the mesh member is operably connected to an inner surface of the distal portion of the first elongate shaft. The mesh member includes a conductive portion configured to contact a surface for ablation.

18 Claims, 8 Drawing Sheets

(56) References Cited

U.S. PATENT DOCUMENTS

| | | |
|---|---|---|
| 6,837,886 B2 | 1/2005 | Collins et al. |
| 7,497,857 B2 | 3/2009 | Briscoe |
| 8,157,796 B2 | 4/2012 | Collins et al. |
| 8,249,685 B2 | 8/2012 | Falwell et al. |
| 2005/0222632 A1 | 10/2005 | Obino |
| 2006/0009756 A1 | 1/2006 | Francischelli et al. |
| 2008/0004534 A1 | 1/2008 | Gelbart et al. |
| 2008/0154256 A1* | 6/2008 | Payne .................. A61B 17/42 606/34 |
| 2008/0281391 A1* | 11/2008 | MacAdam ............ A61B 5/042 607/122 |
| 2010/0256627 A1 | 10/2010 | Ma et al. |
| 2011/0264086 A1* | 10/2011 | Ingle ................ A61B 18/1492 606/33 |
| 2012/0101413 A1 | 4/2012 | Beetel et al. |
| 2012/0265197 A1 | 10/2012 | Truckai et al. |
| 2012/0283715 A1* | 11/2012 | Mihalik ................ A61B 18/02 606/21 |

\* cited by examiner

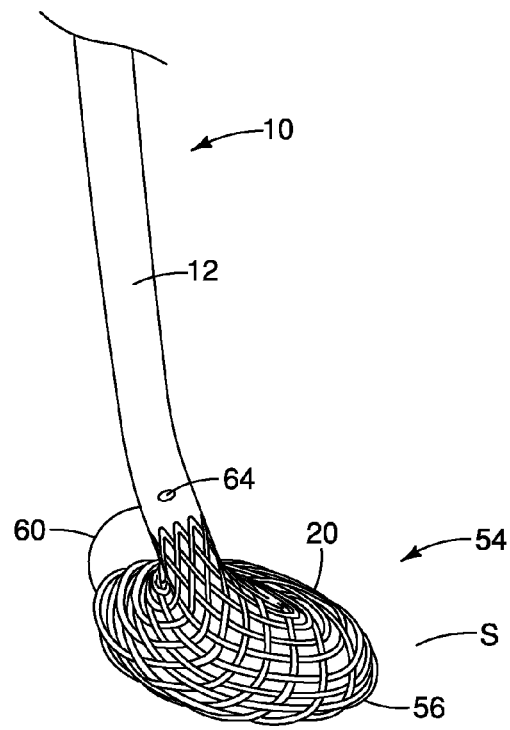
FIG. 7
FIG. 8
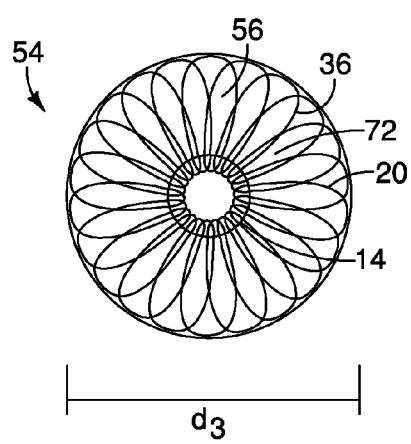
FIG. 9
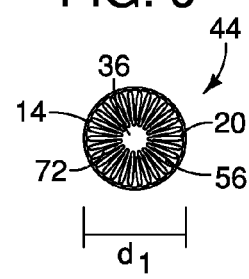

EXPANDABLE MESH PLATFORM FOR LARGE AREA ABLATION

CROSS-REFERENCE TO RELATED APPLICATIONS

This application claims the benefit under 35 U.S.C. § 119 of U.S. Patent Application No. 61/767,067 filed Feb. 20, 2013; which is incorporated by reference in its entirety.

BACKGROUND

Endoscopic treatment of gastrointestinal disorders often requires the need to coagulate tissue for the purpose of hemostasis and/or marking of the tissue. Areas of diseased tissue within the gastrointestinal tract may also be treated using an ablation device. Some ablation devices may be delivered endoscopically.

Radiofrequency ablation (RFA) is one method that can be used to deliver energy for treating or marking the tissue. A bipolar probe is a commonly used RFA device, for example, the Quicksliver Bipolar Probe (Cook Medical, Inc., Bloomington, Ind.) Typical RFA probes are 7 to 10 Fr with electrodes mounted on a ceramic tip on the distal end of the device. One drawback of these probes is that the size of the ablation zone is dependent on the size of the catheter and cannot be altered by the user. In addition, the user must use caution when applying energy when using this type of bipolar probe. Since all the force is distributed across a small (7 or 10 Fr) surface area, an area of high pressure is created increasing the risk of perforation of the tissue at the treatment site.

What is needed in the art is an ablation treatment device that is simple to use, reduces the risk of tissue perforation and is expandable and collapsible to treat larger tissue areas.

BRIEF SUMMARY

Accordingly, it is an object of the present invention to provide a device and a method having features that resolve or improve on one or more of the above-described drawbacks.

An ablation device is provided. In some embodiments, the ablation device includes a first elongate shaft having a proximal portion, a distal portion and a lumen extending at least partially therethrough and a second elongate shaft having a proximal portion, a distal portion and a lumen extending at least partially therethrough. The first elongate shaft is coaxially positioned and longitudinally movable relative to the second elongate shaft. The ablation device further includes a mesh member including a proximal portion and a distal portion. The proximal portion of the mesh member is operably connected to the distal portion of the second elongate shaft and the distal potion the mesh member is operably connected to an inner surface of the distal portion of the first elongate shaft. The mesh member includes a conductive portion configured to contact a surface for ablation.

In some embodiments the ablation device includes a mesh member including a proximal portion and a distal portion, the mesh member having a first diameter and a second diameter greater than the first diameter such that the mesh member is movable to the second diameter by moving the proximal portion relative to the distal portion. The mesh member includes a plastic material and a conductive portion, the conductive portion comprising an ink covering at least a portion of the plastic material and the conductive portion is positionable to contact a surface for ablation.

In another embodiment, a method of ablating a tissue is provided. The method includes inserting a distal portion of an ablation device into a lumen of a patient. The ablation device includes a first elongate shaft having a proximal portion, a distal portion and a lumen extending at least partially therethrough and a second elongate shaft having a proximal portion, a distal portion and a lumen extending at least partially therethrough. The first elongate shaft is coaxially positioned and longitudinally movable relative to the second elongate shaft. The ablation device further includes a mesh member including a proximal portion and a distal portion. The proximal portion of the mesh member is operably connected to the distal portion of the second elongate shaft and the distal potion the mesh member is operably connected to an inner surface of the distal portion of the first elongate shaft. The mesh member includes a conductive portion configured to contact a surface for ablation. The method further includes positioning a portion of the mechanically expandable ablation member at a treatment site, moving the first elongate shaft relative to the second elongate shaft to move the ablation device to an expanded configuration having the second diameter, pressing an end face of the mesh member against the surface and applying energy to the tissue from an energy source.

BRIEF DESCRIPTION OF THE DRAWINGS

FIG. 7 is a partial side view of an embodiment the distal portion of the ablation device;

FIG. 8 is an end view of an end face of an embodiment of the ablation device in an expanded configuration;

FIG. 9 is an end view of an end face of an embodiment of the ablation device in an extended configuration;

DETAILED DESCRIPTION

Figure 1:
FIG. 1 is a partial view of a distal portion of an ablation device in an extended configuration accordance with an embodiment of the present invention.

The invention is described with reference to the drawings in which like elements are referred to by like numerals. The relationship and functioning of the various elements of this invention are better understood by the following detailed description. However, the embodiments of this invention are not limited to the embodiments illustrated in the drawings. It should be understood that the drawings are not to scale, and in certain instances details have been omitted which are not necessary for an understanding of the present invention, such as conventional fabrication and assembly.

As used in the specification, the terms proximal and distal should be understood as being in the terms of a physician delivering the ablation device to a patient. Hence the term "distal" means the portion of the ablation device that is farthest from the physician and the term "proximal" means the portion of the ablation device that is nearest to the physician.

Figure 2:
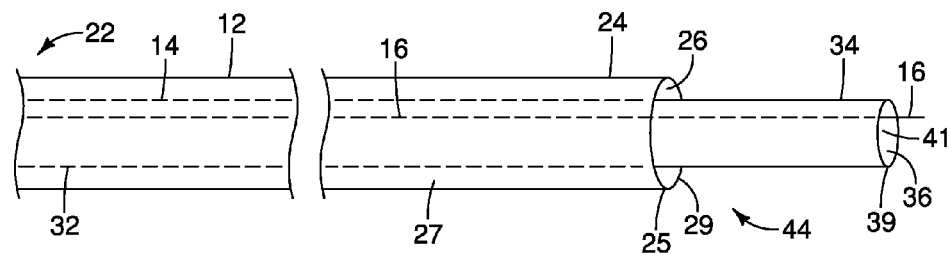
FIG. 2 is partial view of the ablation device shown in FIG. 1 with a mesh member removed.

FIGS. 1 and 2 illustrate an embodiment of an ablation device 10 in accordance with the present invention. The ablation device 10 includes an outer catheter 12, an inner catheter 14, one or more drive cables 16 and a mesh member 20. The inner catheter 14 and the drive cable 16 are shown in FIG. 2 without the mesh member 20 so that the inner catheter 14 and the drive cable 16 can be more readily viewed. The inner catheter 14 may be coaxially positioned within the outer catheter 12 and slidably positionable relative to the outer catheter 12. The outer catheter 12 includes a proximal end portion 22, a distal end portion 24 and a lumen 26 extending at least partially therethrough. The inner catheter 14 includes a proximal end portion 32, a distal end portion 34 and a lumen 36 extending at least partially therethrough. The drive cable 16 is shown extending through the lumen 36 of the inner catheter 14 in FIG. 2. In some embodiments, the drive cable 16 may be positioned external to the inner catheter 14. The drive cable 16 is movable relative to the outer catheter 12 and in some embodiments the drive cable 16 is movable together with the inner catheter 14.

The mesh member 20 is operably connectable to the inner catheter 14, the outer catheter 12 and the drive cable 16. As the inner catheter 14 and the outer catheter 12 are moved relative to each other, the shape of the mesh member 20 changes. In some embodiments, a distal end portion 38 of the mesh member 20 may be extended over a distal end 39 of the inner catheter 14, inverted into the lumen 36 of the inner catheter 14 and operably connected to an inner surface 41 of the distal end portion 34 of the inner catheter 14. The drive cable 16 may also be operably connected to the mesh member 20 and the inner catheter 14 relative to the outer catheter 12. The drive cable 16 may also act as the active wire to transmit current from an electrosurgical unit (ESU) to the mesh member 20 and to the tissue (described in more detail below). A proximal end portion 40 of the mesh member 20 may be operably connected to the distal end portion 26 of the outer catheter 12.

Figure 15:
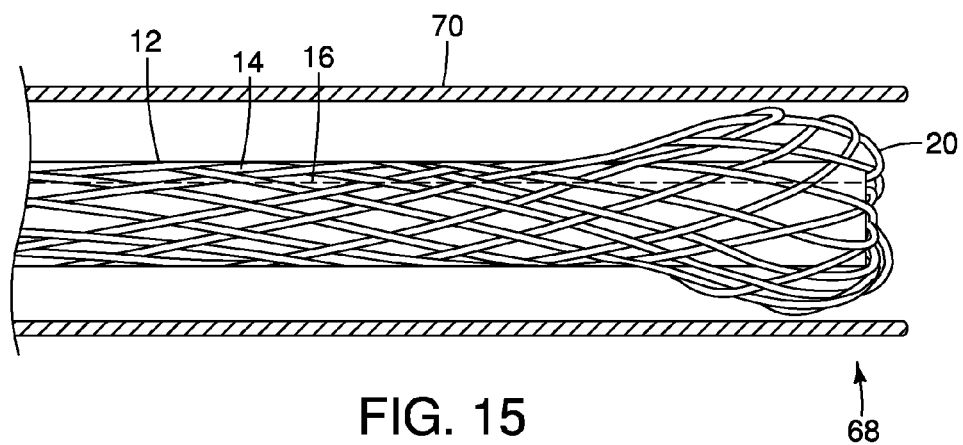
FIG. 15 is a partial sectional view of a distal portion an embodiment of the ablation device.

FIG. 1 illustrates an extended configuration 44 of the device 10 where the distal end portion 36 of the inner catheter 14 is extended distal to the distal end portion 26 of the outer catheter 12 and the mesh member 20 is fully extended so that the mesh member 20 has an outer diameter $d_1$ at a distal portion 46 of an outer surface 48 of the mesh member 20 that is about the same as an outer diameter $d_2$ of the outer catheter 12. The mesh member 20 expands, extends and retracts by longitudinal movement of the inner catheter 14 relative to the outer catheter 12. The ablation device 10 may be delivered to the treatment site with the device 10 in the extended configuration 44. An outer sheath 70 may be positioned over the ablation device 10 for delivery to a treatment site. (See FIG. 15 showing an outer sheath.)

Figure 3:
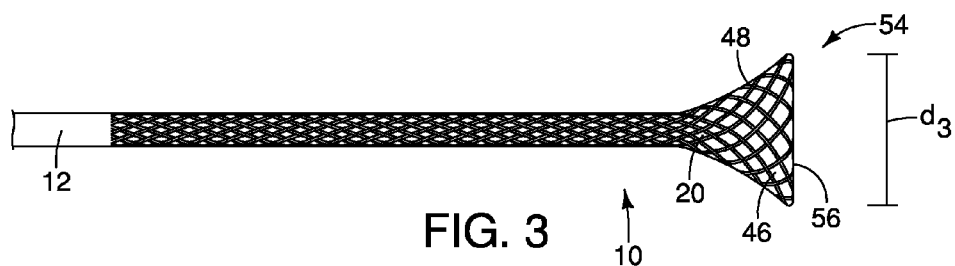
FIG. 3 is a partial view of the ablation device shown in FIG. 1 in an expanded configuration.
Figure 4:
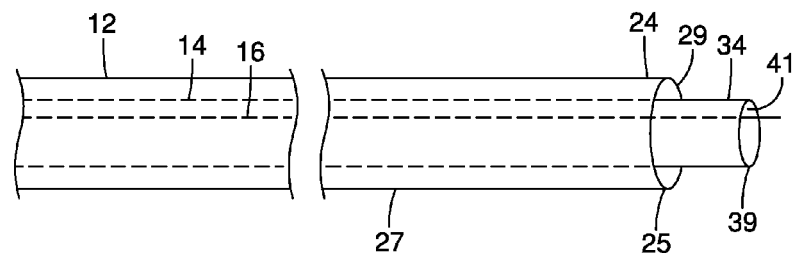
FIG. 4 is a partial view of the ablation device shown in FIG. 3 with the mesh member removed.

FIGS. 3 and 4 illustrate the ablation device 10 in an expanded configuration 54. Similar to FIG. 2 above, FIG. 4 illustrates the outer catheter 12, the inner catheter 14 and the drive cable 16 without the mesh member 20 so that the inner catheter 14 and the drive cable 16 can be more readily viewed. The inner catheter 14 is shown in FIG. 4 proximally withdrawn relative to the position of the inner catheter 14 shown in FIG. 2. The distal end portion 34 of the inner catheter 14 is still distal to but closer to the distal end portion 24 of the outer catheter 12. As shown in FIG. 3, with the inner catheter 14 proximally withdrawn relative to the outer catheter 12 and still having the distal end portion 34 distal to the distal end portion 24, the mesh member 20 is radially expanded relative to the extended configuration 44 and has an outer diameter $d_3$ at the distal portion 46 of the outer surface 48 of the mesh member 20. The outer diameter $d_3$ is greater than the diameters $d_1$ and $d_2$. As shown in FIG. 3, the inner catheter 14 can be withdrawn to the point where an end face 56 of the mesh member 20 forms a generally flattened surface that can be advanced into contact with the tissue at the treatment site.

Figure 5:
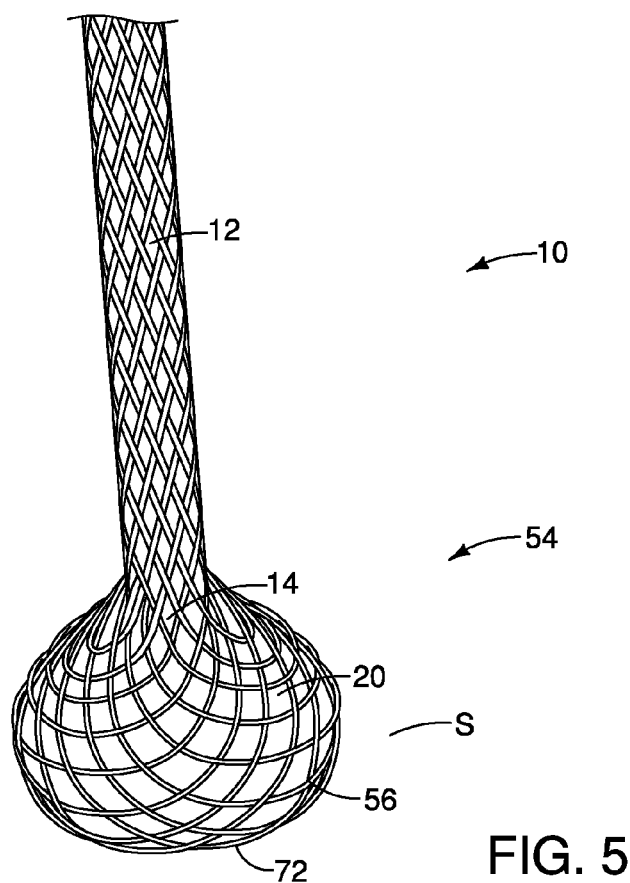
FIG. 5 is a partial view of an embodiment the distal portion of the ablation device.
Figure 6:
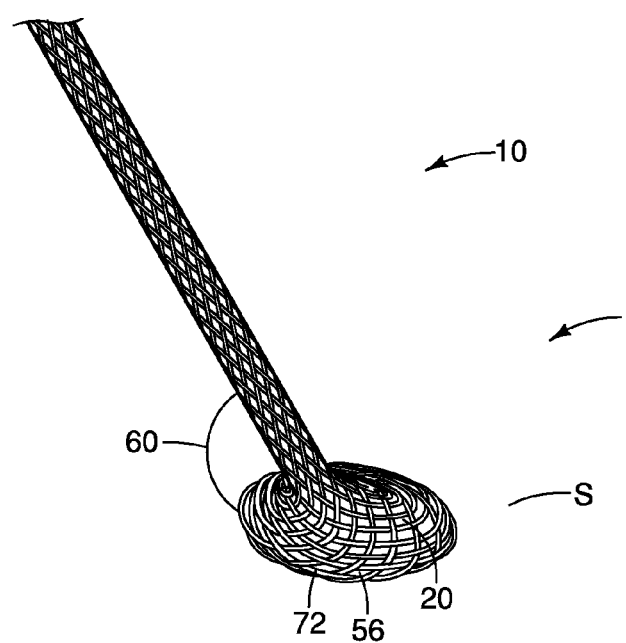
FIG. 6 is a partial side view of an embodiment the distal portion of the ablation device.

FIGS. 5 and 6 illustrate the ablation device 10 in the expanded configuration 54 with the end face 56 of the mesh member 20 flattened against a surface S for treatment. As shown in FIG. 5, the ablation device 10 may be used with the inner and outer catheters 14, 12 generally perpendicular to the treatment surface S. As shown in FIG. 5, the end face 56 is generally flattened against the treatment surface S and can form an ablation disc in the tissue since the end face 56 of the mesh member 20 can directly contact the tissue across the entire surface of the end face 56. The end face 56 can be pressed against the tissue and generally flattened without application of undue force to flatten the end face 56. The risk of perforation of the tissue is also reduced due to the decreased pressure and to the spreading of the energy across the end face 56.

FIG. 6 illustrates the ablation device 10 in the expanded configuration 54 with the end face 56 flattened against a surface S for treatment. In some embodiments, the mesh member 20 is made of a flexible material that allows the end face 56 of the mesh member 20 to contact the surface S for treatment with the inner catheter 14 and the outer catheter 12 positioned at an oblique angle 60 relative to the surface S. By way of non-limiting example, the mesh member 20 may be formed of a plastic material coated with a conductive material (described in more detail below) that is flexible enough to bend and flatten the end face 56 against the surface S by moving the mesh member 20. In some embodiments, the ablation device 10 may include a hinge 64 as shown in FIG. 7 to facilitate positioning of the end face 56 against the surface S. As shown in FIG. 7, the outer catheter 12 to be extended generally perpendicular to the surface S for treatment and the hinge 64 allows the mesh material 20 to bend at the oblique angle 60 so that the end face 56 of the mesh material 20 is positioned flat against the surface S for treatment of the tissue. In some embodiments, the hinge 64 may be on the inner catheter 14 and the outer catheter 12. The hinge 64 may be used with mesh materials that are formed from stiffer materials, for example some metal meshes may be too rigid to deform easily against the surface S and would require too much pressure against the surface S to flatten the end face 56. The hinge 64 may be any kind of a hinge that allows the ablation device 10 to be delivered to the site, bent at an angle and then returned to the generally straight configuration for withdrawal from the patients. The bending at an angle and return of the ablation device 10 to the straightened position may be by mechanical means such as a drive cable or by contact with a portion of the body lumen.

An end view of the end face 56 of the mesh member 20 in the expanded configuration 54 is shown in FIG. 8. The entire end face 56 may be energized for treatment of tissue or portions of the end face 56 may be energized as describe in more detail below. The end face 56 is shown as having a generally circular face, however other shapes may also be used. By way of non-limiting example, other shapes for the end face 56 may be formed by changing the weave pattern of the mesh member 20, for example forming an oval or a ring. The weave pattern may be varied to also change the overall size of the end face 56 to create a different size treatment area. In some embodiments, the density of the weave pattern or the thickness of the woven portions may also be varied to change the energy delivered to the treatment area and the flexibility of the mesh material 20. The size of the inner catheter 12 and the attachment of the mesh member 20 may also contribute to the size, density and energy delivery of the end face 56. As shown in FIG. 8, the mesh member 20 may be folded over the distal end portion 34 of the inner catheter 14 and extend into the lumen 36 and be connected to the inside of the catheter 14. The mesh member 20 may extend across a portion of the lumen 36 so that the end face 56 may be used to ablate an entire disc of tissue. In some embodiments, the lumen 36 may be at least partially free from the mesh member 20 if a ring is desired for the treatment area.

FIG. 9 illustrates an end view of the end face 56 of the mesh member 20 in the extended configuration 44. The diameter $d_1$ and thus the surface area of the end face 56 in the extended configuration 44 is smaller than the diameter $d_3$ of the end face 56 in the expanded configuration 54. The ablation device 10 may be used in the extended configuration 44 so that the end face 56 is energized to treat a smaller tissue area. In some embodiments, the mesh member 20 may be configured so that the end face 56 may be energized or a portion of the outer surface 48 of the mesh member 20 may be energized with the ablation device 10 in the extended configuration 44 (See also FIG. 1.) The mesh may be formed from wire such as nickel titanium alloys, for example, nitinol, stainless steel, cobalt alloys and titanium alloys. In some embodiments, the mesh may be formed from a polymeric material such as a polyolefin, a fluoropolymer, a polyester, for example, polypropylene, polytetrafluoroethylene, polyvinylidene fluoride, polyethylene terephthalate (PET), and combinations thereof. Other materials known to one skilled in the art may also be used to form the mesh member 20.

Figure 10:
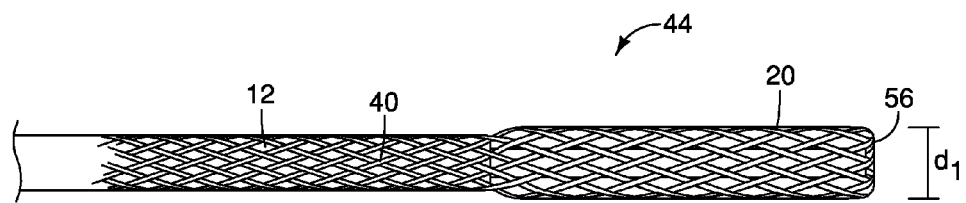
FIGS. 10-13 show a partial view of a distal portion of an embodiment of the ablation device moving from an extended configuration to an expanded configuration to a retracted configuration.
Figure 11:
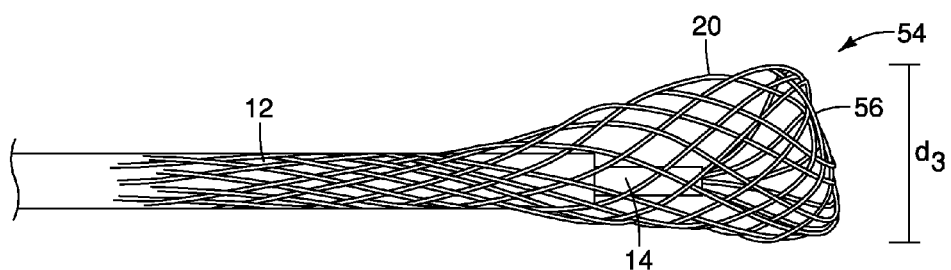
Figure 12:
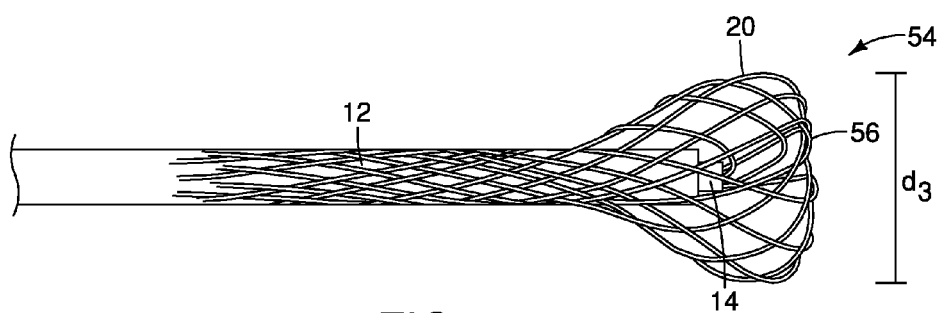

FIGS. 10 to 13 illustrate movement of the mesh member 20 of the ablation device 10. As shown in FIGS. 10 to 13, the mesh member 20 is moved by moving the inner catheter 14 relative to outer catheter 12 so that distal end portion 34 of the inner catheter 14 is moved closer to the distal end portion 24 of the outer catheter 12. The drive cable 16 may also be used to move the inner catheter 14 relative to the outer catheter 12. The ablation device 10 is in the extended configuration 44 shown in FIG. 10 with the inner catheter 14 extended to its distalmost position relative to the outer catheter 12 so that the mesh member 20 is fully distally extended. FIGS. 11 and 12 show the inner catheter 14 being proximally withdrawn relative to the outer catheter 12 and the mesh member 20 expanding to the expanded configuration 54 and the diameter of the end face 56 increasing relative to the diameter of the end face 56 shown in FIG. 10. The drive cable 16 remains connected to the mesh member 20 in all the configurations so that the ablation device 10 may be energized in any of the positions shown in FIGS. 10-12. In FIGS. 10-12, the distal end portion 34 of the inner catheter 14 is distal to the distal end portion 24 of the outer catheter 12.

Figure 13:
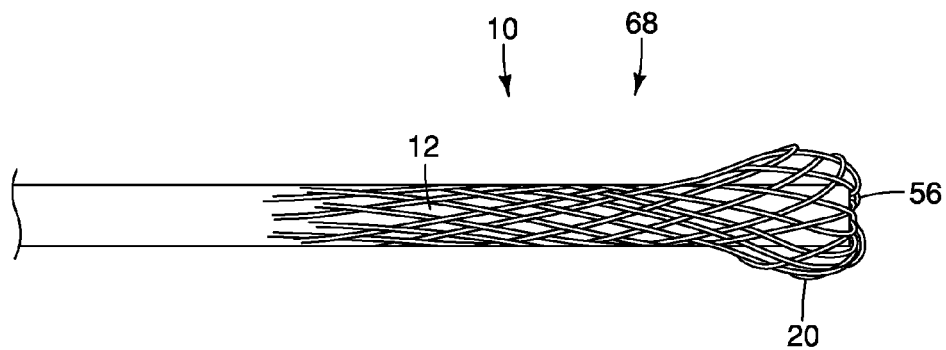

FIG. 13 illustrates the mesh member 20 in a retracted configuration 68 where the inner catheter 14 is positioned within the outer catheter 12 so that the distal end portion 24 of the inner catheter 14 is positioned proximal to a distal end 25 of the outer catheter. The mesh member 20 extends over a distal end 29 of the outer catheter 12. The distal end portion 38 of the mesh member 20 is withdrawn into the lumen 26 of the inner catheter 14 and the proximal end portion 40 of the mesh member 20 remains connected to an outer surface 27 of outer catheter 12. The ablation device 10 may be moved to the retracted configuration 68 by proximally withdrawing the drive cable 16 and/or the inner catheter 14 relative to the outer catheter 12. The retracted configuration 68 may be used to deliver the ablation device 10 to the treatment site. The ablation device 10 may also be moved to the retracted configuration 68 from the extended or expanded configurations 44, 54 to facilitate removal of tissue that may be adhered or caught in the mesh member 20 after the tissue has been ablated. The ablation device 10 may be returned to the extended or expanded configuration 44, 54 by moving the inner catheter 14 distally relative to the outer catheter 12 if additional treatments are desired. The ablation device 10 may be "cleaned" by proximal withdrawal of the inner catheter 14 relative to the outer catheter 12 and repositioned by distally moving the inner catheter 14 relative to the outer catheter 12 as many times as needed for a treatment procedure.

Figure 14:
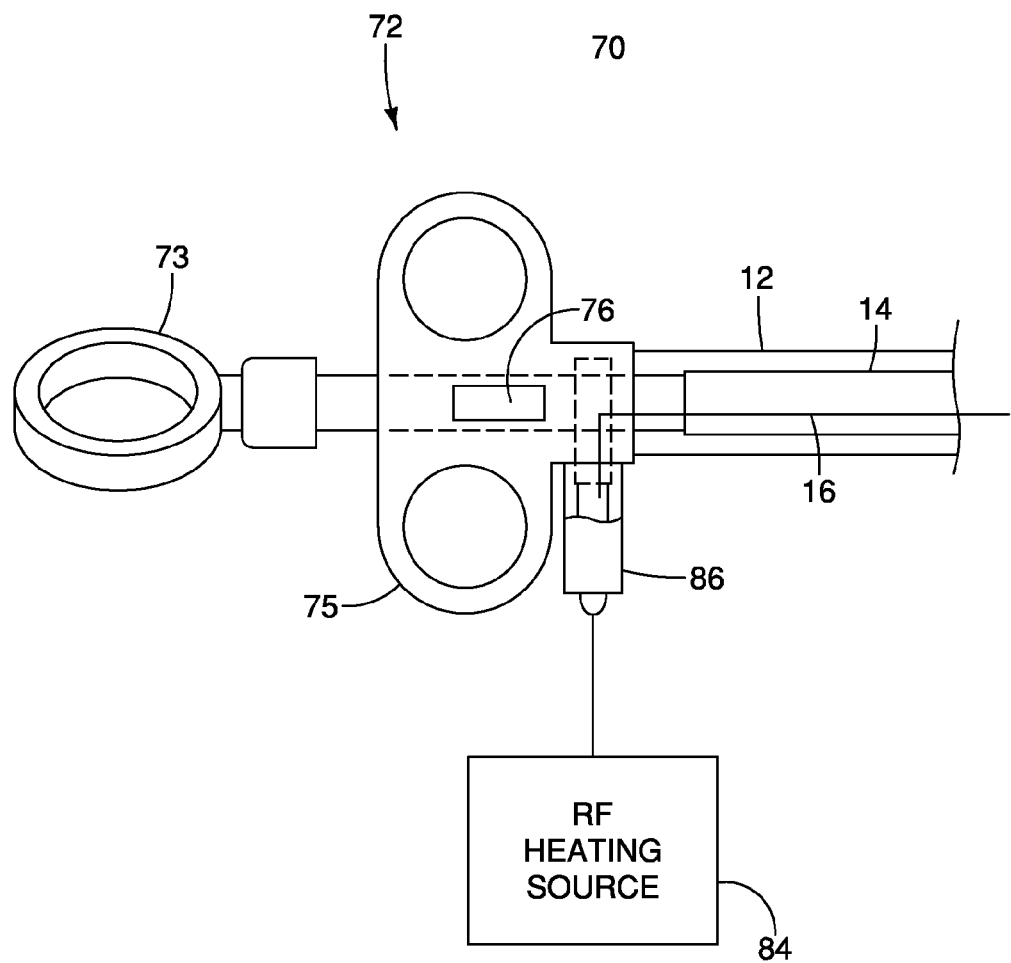
FIG. 14 is a partial view of a proximal portion of an embodiment of the ablation device.

A control handle 70 is provided at a proximal portion 72 of the ablation device 10. An exemplary control handle 70 is shown in FIG. 14 and one skilled in the art will recognize that other types of handles suitable for moving the inner catheter 14 relative to the outer catheter 12 may also be used. By way of non-limiting example, the handle 70 includes a first portion 73 and a second portion 75 that move relative to each other. As shown in FIG. 14, the first portion 73 is operably connected to the inner catheter 14. The second portion 75 is operably connected to the outer catheter 12. The first portion 73 may be moved proximally and/or the second portion 75 may be moved distally to move the inner catheter 14 relative to the outer catheter 12 to move the mesh member 20.

The handle 70 may include a lock 76 shown in FIG. 14 to releasably lock the first portion 73 in position relative to the second portion 75 and thus lock the mesh member 20 in position. The lock 76 may releasably lock the first and second portions 73, 75 of the handle 70 together at any proximal/distal positioning of the inner and outer catheters 14, 12 so that the mesh member 20 may be locked at any size and any position that is suitable for the treatment site. FIG. 7 also illustrates an energy source 84. As shown in FIG. 14, the handle 70 may include a connector 86 for operably connecting one or more of the drive cables 16 to the energy source 84 to operably connect the energy source 84 to the mesh member 20. A separate wire may also be used to connect to the energy source 84 so that the mesh member is operably connected to the energy source 84 to supply energy to the mesh member 20 for ablation of the tissue. In some embodiments, the energy source 84 may be a radio frequency source. However, other types of energy sources 84 may also be used to provide energy to the mesh member 20. By way of non-limiting example, additional possible energy sources may include microwave, ultraviolet, cryogenic and laser energies.

In some embodiments, the ablation device 10 may include an outer sheath 70 that is positionable over the outer catheter 12 and the mesh member 20 when the ablation device is in the retracted configuration 68 as shown in FIG. 15 or in the extended configuration 54 (not shown). The outer sheath 70 may be included to facilitate delivery of the ablation device 10 to a treatment site and to withdraw the ablation device 10 after treatment.

Figure 16:
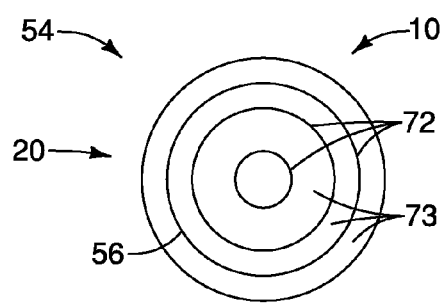
FIG. 16 is an end view of an end face of an embodiment of the ablation device.

In some embodiments, the ablation device 10 may be provided as a monopolar device or a bipolar device where the mesh member 20 includes a conductive portion 72. The mesh member 20 itself, when formed from an electrically conductive material may be the conductive portion 72 or portions of the mesh member 20 may be conductive portions 72 with non-conductive portions 73 being coated with an insulating material. For example, in a bipolar ablation device 10, an insulating material is used between the active and return portions. The insulating material can also be used to form patterns for ablation, where conductive portions 72 of the mesh member 20 may be activated and non-conductive portions 73 of the mesh member 20 remain inactive. See for example, FIG. 16 illustrating an embodiment of the ablation device 10 showing the end face 56 of the mesh member 20 having conductive portions 72 separated by non-conductive portions 73. The non-conductive portions 73 may be provided between conductive portions 72 of the mesh member 20 and the space between the conductive portions 72 may be optimized to control the depth of ablation of the target tissue. Spacing distances between the conductive portions 72 may be optimized depending on such factors as the type of target tissue, the depth of the lesion, the type of energy and the length of application of the energy to the tissue.

In some embodiments, the conductive portions 72 of the mesh member 20 may comprise conductive ink that is applied to the exterior of the mesh member 20. The conductive ink may be applied in any pattern and spacing to be used for tissue treatment. In some embodiments, the conductive ink may be a silver-based ink. An exemplary silver-based ink may be obtained from Conductive Compounds (product number AG-510, Hudson, N.H.). However, other types of conductive ink may also be used, such as platinum-based, gold-based and copper-based inks. The inks may be epoxy-based inks or non-epoxy inks, such as urethane inks. In some embodiments, the active portions of the mesh member 20 may comprise conductive polymers. The conductive ink may be applied to the mesh member 20 with a variety of printing processes, such as pad printing, ink jet printing, spraying, marker striping, painting or other like processes. In some embodiments, the conductive ink may be applied to the mesh member with by spraying, dipping, painting or an electrostatic coating process.

The non-conductive portion 73 of the mesh member 20 may be an insulating portion to separate conductive portions 72 of the mesh member 20. In some embodiments, a coating may be applied to the mesh member 20 to form the non-conductive portions 73 in a quantity that is sufficient to insulate the conductive portions 72 from each other or to coat portions of the mesh member 20 when the mesh member 20 itself is formed of a conductive material. In some embodiments, the insulating coating may be made from parylene-N (poly-p-xylylene). Other xylylene polymers, and particularly parylene polymers, may also be used as a coating within the scope of the present invention, including, for example, 2-chloro-p-xylylene (Parylene C), 2,4-dichloro-p-xylylene (Parylene D), poly(tetraflouro-p-xylylene), poly(carboxyl-p-xylylene-co-p-xylylene), fluorinated parylene, or parylene HT® (a copolymer of perfluorinated parylene and non-fluorinated parylene), alone or in any combination. Preferred coatings will include the following properties: low coefficient of friction (preferably below about 0.5, more preferably below about 0.4, and most preferably below about 0.35); very low permeability to moisture and gases; fungal and bacterial resistance; high tensile and yield strength; high conformality (ready application in uniform thickness on all surfaces, including irregular surfaces, without leaving voids); radiation resistance (no adverse reaction under fluoroscopy); bio-compatible/bio-inert; acid and base resistant (little or no damage by acidic or caustic fluids); ability to be applied by chemical vapor deposition bonding/integrating to wire surface (bonding is intended to contrast to, for example, fluoroethylenes that form surface films that are able to be peeled off an underlying wire); and high dielectric strength.

Figure 17A:
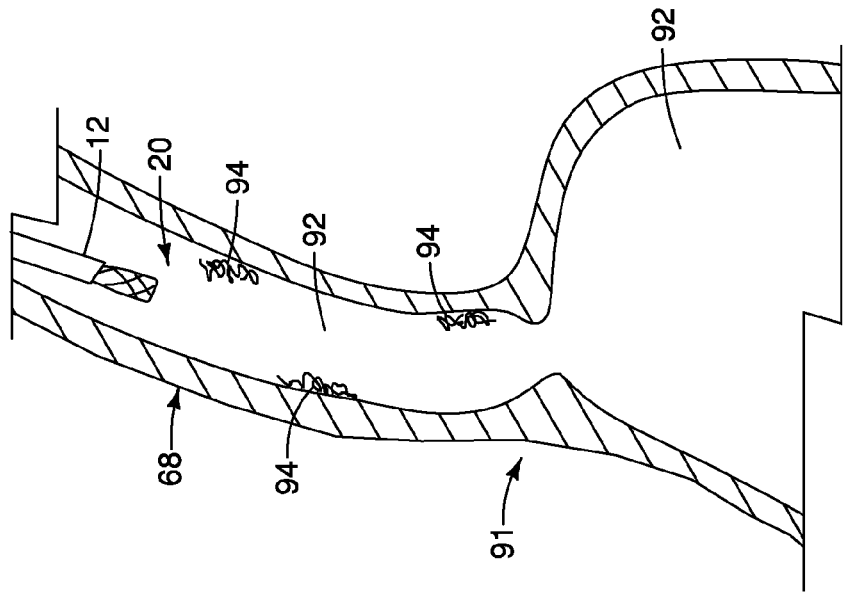
FIGS. 17A-17C illustrate operation of the ablation device.
Figure 17B:
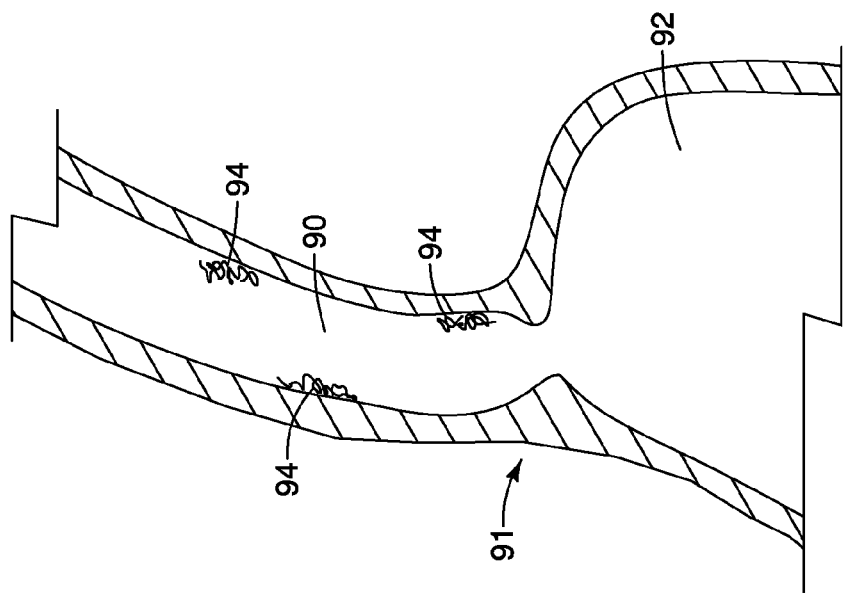
Figure 17C:
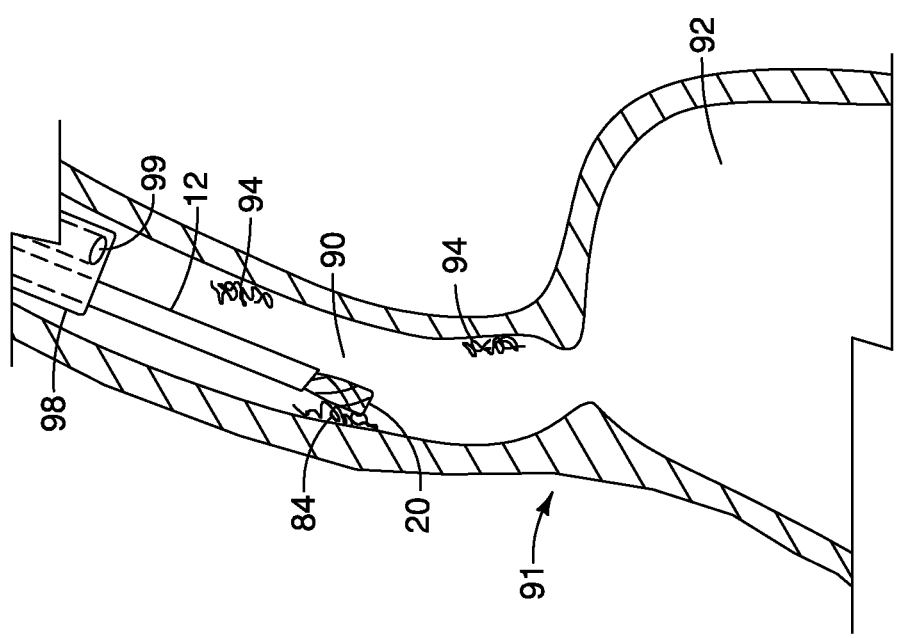

Operation of the ablation device 10 will be explained with reference to FIGS. 17A-17C. FIG. 18A illustrates a patient's esophagus 90, lower esophageal sphincter (LES) 91 and stomach 92. Areas of diseased tissue 94 within the esophagus 90 are also shown. FIG. 17B illustrates the mesh member 20 of the ablation device 10 in the retracted configuration 68 being inserted into the patient's esophagus 80 for delivery to the proper position. The inner catheter 14 is positioned within the outer catheter 12 for advancement to the tissue. In some situations, the ablation device 10 may be delivered using an endoscope 98 that is shown in FIG. 17C to facilitate placement of the mesh member 20 in the proper position to ablate the diseased tissue 94. The endoscope 98 may include a viewing port 99 for visualizing the diseased tissue 94 and positioning the ablation device 10. The ablation device 10 may be delivered through the working channel or optionally back-loaded into the working channel of the endoscope before insertion of the endoscope 98 into the patient. As shown in FIG. 17C, the mesh member 20 of the ablation device ablation device 10 is delivered through the endoscope 98 and positioned so that the mesh member 20 is adjacent to the diseased tissue 94 in the expanded configuration 54. The mesh member 20 may be positioned so that the end face 56 of the mesh member 20 directly contacts the diseased tissue 94 or an electroconductive fluid may be provided between the end face 56 and the diseased tissue 94. The power source 84 is activated for a sufficient time to ablate the diseased tissue 94. The mesh member 20 may then be proximally withdrawn to the retracted configuration 68 by proximally moving the inner catheter 14 relative to the outer catheter 12. The mesh member 20 may be repositioned at a new tissue site or removed once the ablation of the diseased tissue is completed. While the procedure has been described with reference to the ablation of diseased tissue in the esophagus using the ablation device 10, the location of the treatment is not limited to the esophagus. By way of non-limiting example, portions of the stomach, the gastrointestinal tract, the lungs or the vascular system may also be treated using the ablation device 10. For example, the device 10 may be used for treating bleeding varices in the esophagus or for treatment of prostatic diseases, such as benign prostatic hyperplasia.

The above Figures and disclosure are intended to be illustrative and not exhaustive. This description will suggest many variations and alternatives to one of ordinary skill in the art. All such variations and alternatives are intended to be encompassed within the scope of the attached claims. Those familiar with the art may recognize other equivalents to the specific embodiments described herein which equivalents are also intended to be encompassed by the attached claims.

The invention claimed is:

1. An ablation device comprising:
a first elongate shaft having a proximal portion, a distal portion and a lumen extending at least partially therethrough;
a second elongate shaft having a proximal portion, a distal portion and a lumen extending at least partially therethrough, the first elongate shaft coaxially positioned and movable relative to the second elongate shaft; and
a mesh member comprising a proximal portion and a distal portion, the proximal portion of the mesh member operably connected to the distal portion of the second elongate shaft and the distal portion of the mesh member extending distally past a distal end of the first elongate shaft, folding proximally and extending into the lumen of the first elongate shaft and operably connected to an inner surface of the distal portion of the first elongate shaft, the mesh member having a first diameter and a second diameter greater than the first diameter such that the mesh member is movable to the second diameter by moving the first elongate shaft relative to the second elongate shaft and the mesh member comprising a conductive portion configured to contact a surface for ablation.

2. The ablation device according to claim 1, wherein the proximal portion of the mesh member is connected to an outer surface of the second elongate shaft.

3. The ablation device according to claim 1, wherein the mesh member is proximally retractable so that the distal portion of the mesh member is withdrawn into the lumen of the second elongate shaft in a retracted configuration.

4. The ablation device according to claim 1, wherein the mesh member comprises an end face at a distal-most end of the ablation device configured to contact the surface for ablation.

5. The ablation device according to claim 4, wherein the end face is configured to contact the surface for ablation at an angle relative to a longitudinal axis of the first and second elongate shafts.

6. The ablation device according to claim 5, wherein the ablation device further comprises a hinge configured to allow the end face to contact the surface for ablation at the angle.

7. The ablation device according to claim 4, wherein the end face has a generally circular or oval shape.

8. The ablation device according to claim 4, wherein a surface of the end face extending across the second diameter is configured to contact the surface for ablation.

9. The ablation device according to claim 1, wherein the mesh material comprises a plastic material.

10. The ablation device according to claim 1, wherein the conductive portion comprises a conductive ink.

11. The ablation device according to claim 1, further comprising a power source operably connected to the mesh member.

12. The ablation device according to claim 1, wherein the ablation device is a bipolar device.

13. The ablation device according to claim 1, wherein the mesh member comprises a non-conductive portion.

14. The ablation device according to claim 1, wherein the ablation device comprises an extended configuration wherein the mesh member has substantially the first diameter and an end face configured to contact the surface for ablation.

15. The ablation device according to claim 1, wherein the distal portion of the mesh member extends distal to a distal end of the second elongate shaft.

16. The ablation device according to claim 1, wherein a portion of the mesh member extends over an outer surface of the first elongate shaft and an outer surface of the second elongate shaft.

17. The ablation device according to claim 1, wherein the first elongate shaft is coaxially movable within the lumen of the second elongate shaft.

18. The ablation device according to claim 1, comprising a cable operably connected to the mesh member.

* * * * *